(12) United States Patent
Zeng et al.

(10) Patent No.: US 8,366,743 B2
(45) Date of Patent: *Feb. 5, 2013

(54) HEART SEPTAL DEFECT OCCLUSION DEVICE

(75) Inventors: Weijun Zeng, Shenzhen (CN); Deyuan Zhang, Shenzhen (CN); Eric Zi, Shenzhen (CN)

(73) Assignee: Lifetech Scientific (Shenzhen) Co., Ltd (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/927,194

(22) Filed: Nov. 8, 2010

(65) Prior Publication Data

US 2011/0066180 A1 Mar. 17, 2011

Related U.S. Application Data

(63) Continuation-in-part of application No. 11/307,178, filed on Jan. 26, 2006, now Pat. No. 7,828,818.

(30) Foreign Application Priority Data

Jan. 28, 2005 (CN) .......................... 2005 1 0032924

(51) Int. Cl.
*A61B 17/08* (2006.01)
(52) U.S. Cl. .................. 606/213; 606/151; 606/157
(58) Field of Classification Search .................. 606/213, 606/151, 200, 232, 131; 623/23.72
See application file for complete search history.

(56) References Cited

U.S. PATENT DOCUMENTS

| | | | |
|---|---|---|---|
| 3,874,388 A | 4/1975 | King et al. | |
| 5,152,777 A * | 10/1992 | Goldberg et al. | 606/200 |
| 5,451,235 A | 9/1995 | Lock et al. | |
| 5,593,441 A * | 1/1997 | Lichtenstein et al. | 600/37 |
| 5,683,411 A | 11/1997 | Kavteladze et al. | |
| 5,944,738 A | 8/1999 | Amplatz et al. | |
| 6,063,113 A * | 5/2000 | Kavteladze et al. | 623/1.15 |
| 6,273,901 B1 * | 8/2001 | Whitcher et al. | 606/200 |
| 6,712,836 B1 | 3/2004 | Berg et al. | |
| 7,144,410 B2 | 12/2006 | Marino et al. | |
| 7,658,748 B2 | 2/2010 | Marino et al. | |
| 2002/0156499 A1 * | 10/2002 | Konya et al. | 606/213 |
| 2004/0117032 A1 | 6/2004 | Roth | |
| 2005/0065547 A1 | 3/2005 | Marino et al. | |
| 2006/0095068 A1 * | 5/2006 | WasDyke et al. | 606/200 |
| 2006/0217760 A1 * | 9/2006 | Widomski et al. | 606/213 |

FOREIGN PATENT DOCUMENTS

| | | |
|---|---|---|
| CN | 2430113 | 5/2001 |
| CN | 2566817 | 8/2003 |
| CN | 1442122 | 9/2003 |
| CN | 2661130 | 12/2004 |
| WO | WO 2005/034738 A | 4/2005 |

* cited by examiner

*Primary Examiner* — Corrine M McDermott
*Assistant Examiner* — Alexander Orkin
(74) *Attorney, Agent, or Firm* — Raymond Sun

(57) ABSTRACT

An occlusion device has a right disc made from a metal mesh having a plurality of openings, and a left disc having at least two skeletons that are covered by a membrane. Each skeleton passes through openings of the metal mesh to interlock the right and left discs, and a coil is wrapped around each opposing end segment of the skeletons. The skeletons can have a looped section where the skeleton is twisted or looped to cross or overlap itself. In addition, each skeleton can be formed from a braided strand of a plurality of wires.

20 Claims, 8 Drawing Sheets

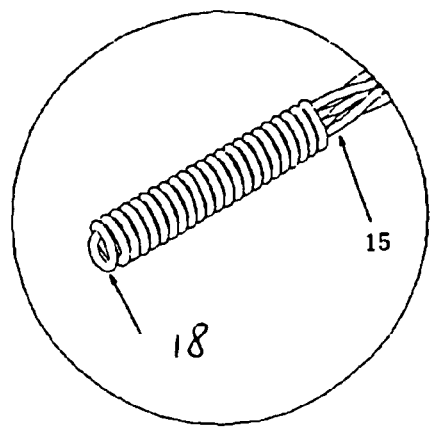
FIG. 20
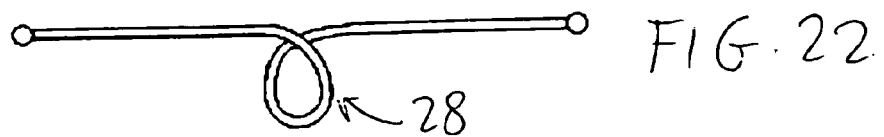
FIG. 22
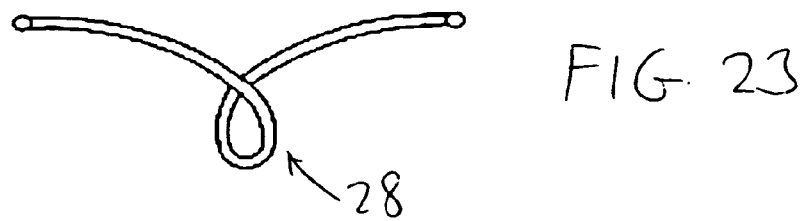
FIG. 23
FIG. 24
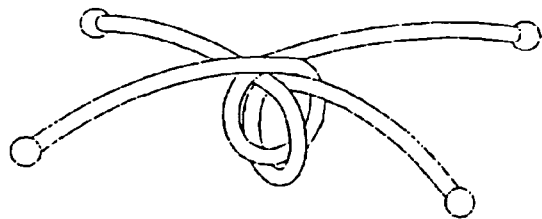

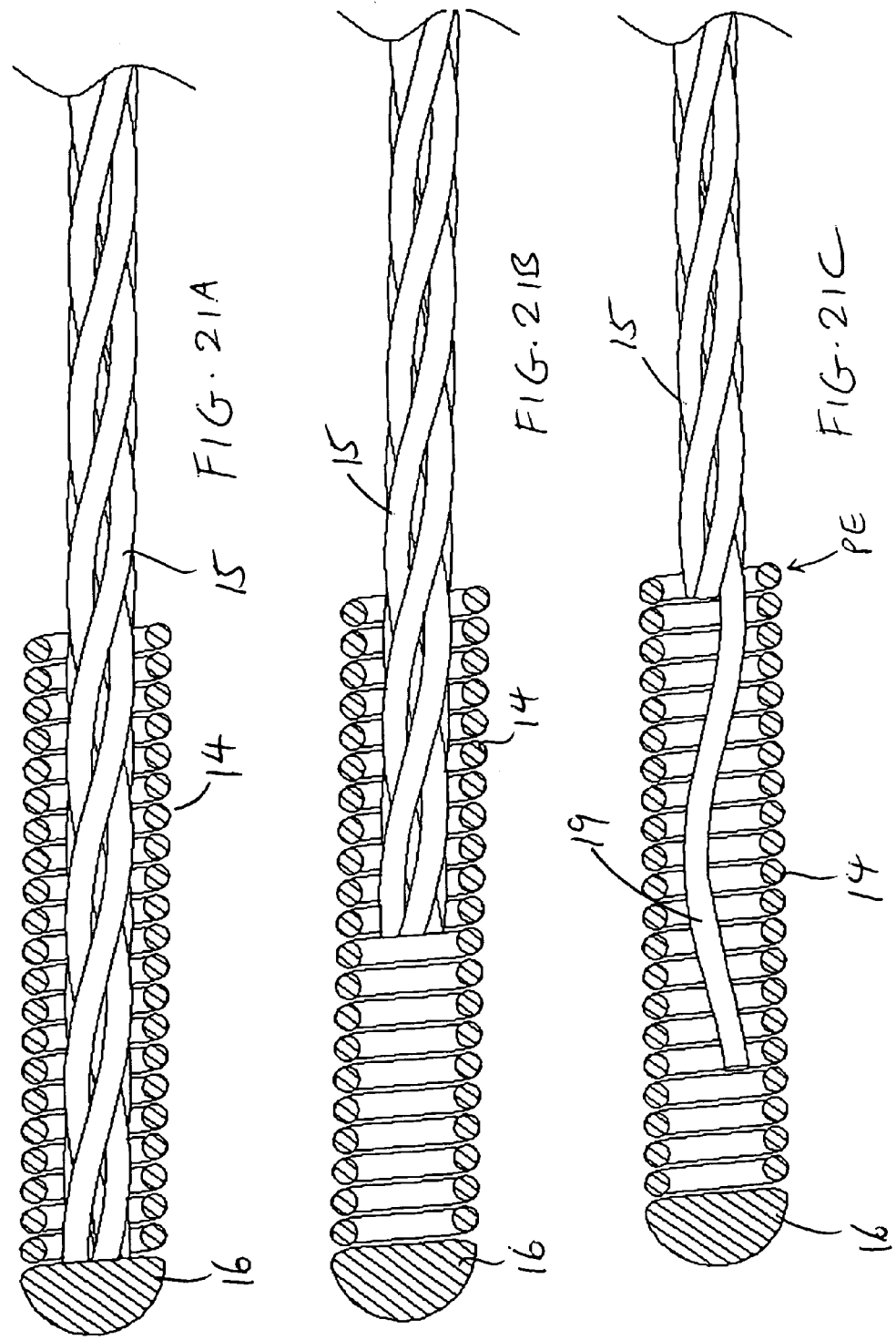

HEART SEPTAL DEFECT OCCLUSION DEVICE

RELATED CASES

This is a continuation-in-part of application Ser. No. 11/307,178, now U.S. Pat. No. 7,828,818, filed Jan. 26, 2006, which claims the benefit of a Chinese patent application No.20051 0032924.0 (CN), filed on Jan. 28, 2005.

BACKGROUND OF THE INVENTION

1. Field of the Invention

The present invention relates to an occlusion device for treating congenital heart disease, such as patent foramen ovale (PFO), atrial septal defect (ASD), patent ductus arteriosus (PDA) or ventricular septal defect (VSD), etc.

2. Description of the Prior Art

Congenital heart diseases include patent foramen ovale (PFO), atrial septal defect (ASD), patent ductus arteriosus (PDA) and ventricular septal defect (VSD), etc. PFO and ASD are openings in the wall between the right atrium and left atrium of the heart thereby creating the possibility that the blood could pass from the right atrium to the left atrium. But the defect size of PFO is usually smaller than that of ASD and the defect will not extend perpendicularly to the septal wall, i.e. left atrial septal defect is not concentric with that of the right atrium. Once the occluder has been placed, it will prevent the thrombus from entering into the left atrium. Furthermore, the atrial septal defect (ASD) is usually larger and requires repair. Currently there are many types of endocardiac occlusion devices for treating congenital heart diseases. These occluders are delivered to the desired location by a corresponding catheter.

Mechanical occlusion devices for treating congenital heart diseases have been proposed in the past, some of which are disclosed in Franker et al., Chinese patent application No. 97194488.1; Franker et al., Chinese patent application No. 98808876.2; and Michael et al., and Chinese patent application No. 98813470.5. This kind of device includes a support mesh with contractibility and biocompatible materials, and the biocompatible materials are connected to the circumference of the support mesh. The support mesh, which is put into the catheter first, is delivered to the desired location, and then is deployed to close the septal defect. This kind of device is easy to withdraw and has excellent centricity. However, the left disc of this device directly contacts blood, so that it can form thrombus and release harmful metallic elements more easily. Moreover, because the two discs are a whole, they cannot automatically adjust the angle to adapt to the unique anatomy of the patient. Meanwhile, if the left disc is not deployed completely, the operation becomes more complicated. In addition, with the existing technique and the operation method, it is very difficult to determine the size and shape of the septal defect precisely, as well as the limit of the waist size, thereby causing many difficulties to physicians, such as selection error, etc. If an oversized device is selected, the occluder will form a cucurbit shape, and result in an imperfect closing effect.

Accordingly, it would be advantageous to provide a reliable occlusion device which can automatically adjust the angle to adapt to the unique anatomy of the patient.

SUMMARY OF THE DISCLOSURE

The present invention provides a reliable occlusion device with adjustable length tether which can adapt the interseptal length of the device to the unique anatomy of the patient. The two discs can attach to the septal defect closely, so they can improve the closing ability. Moreover, thrombus can be reduced because its left disc is covered with membranes and operates more easily.

The present invention provides an occlusion device where the right disc is made from a double-deck wire mesh with contraction function, and the left disc is made from at least two skeletons covered with membranes, and the two discs are adaptively interlocked together by the skeletons passing through the mesh of the right disc.

The middle segment of each skeleton is U-shaped, and the depths of the U trough are different, so the skeleton can form a plane after being linked together. The skeleton is then covered with membranes to form a disc shape.

The left disc is made from several radially-extending skeletons by heat treatment, and covered with membranes, and the center of each skeleton extends radially after overlapping together.

The two ends of each skeleton are spherical shaped and are wrapped by the membranes, and the ends of the right disc are fixed by a tip or a joint, then the right disc undergoes heat treatment. Then the skeletons pass through the mesh near the joint and are overlapped together. The membranes are made from biocompatible materials.

Furthermore, because the connection of the two discs has a gimbal function and the distances between the two discs may expand and contract suitably, the device can adapt to the interseptal length between two discs for the unique anatomy of the patient. Therefore, the two discs may attach to the heart defects closely and increase its closing ability. Moreover, the occlusion device can reduce the thrombus as well as harmful elements because of its left disc being covered with membranes. In addition, the device, which is a fission structure (i.e. its two discs could deploy completely), is easy to operate and increases the closing reliability.

In accordance with another embodiment of the present invention, the occlusion device has a right disc made from a metal mesh, the metal mesh having a plurality of openings, and a left disc comprising at least two skeletons that are covered by a membrane. Each skeleton passes through openings of the metal mesh to interlock the right and left discs, and each skeleton has opposing end segments, with a coil wrapped around each end segment.

In accordance with yet another embodiment of the present invention, the skeletons have a looped section where the skeleton is twisted or looped to cross or overlap itself.

In accordance with yet a further embodiment of the present invention, each skeleton is formed from a braided strand of a plurality of wires.

BRIEF DESCRIPTION OF THE DRAWINGS

FIG. 20 illustrates the completed coil of the device of FIG. 19.

FIGS. 21A, 21B and 21C are cross-sectional views illustrating the construction of the end segments of the skeleton of FIG. 16 according to three different embodiments thereof.

FIG. 22 illustrates a modified skeleton with a looped segment.

FIG. 23 illustrates the bending of the skeleton of FIG. 22.

FIG. 24 is a perspective view of two skeletons of FIG. 22 being combined together.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
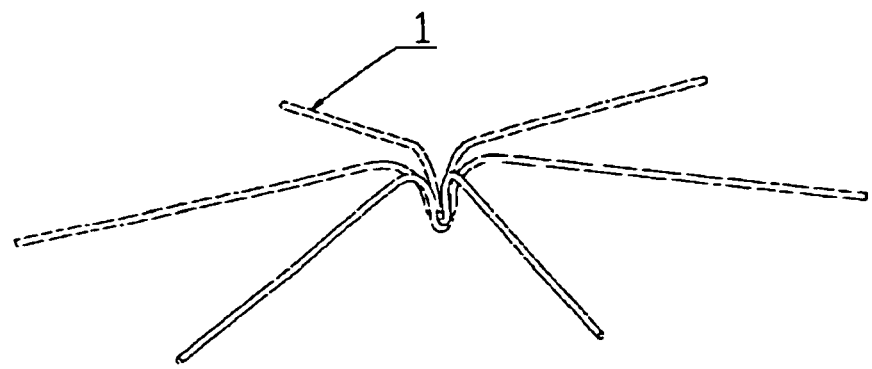
FIG. 1 is a schematic representation of a disc which is constructed by skeletons in accordance with the invention.
Figure 2:
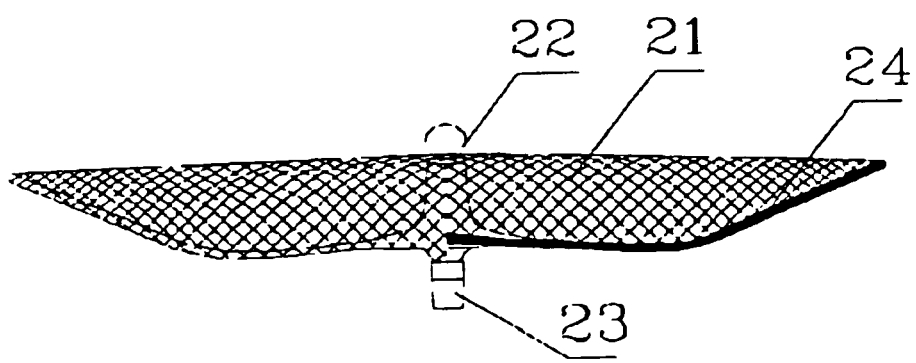
FIG. 2 is a side view of the right disc in accordance with the invention.
Figure 4:
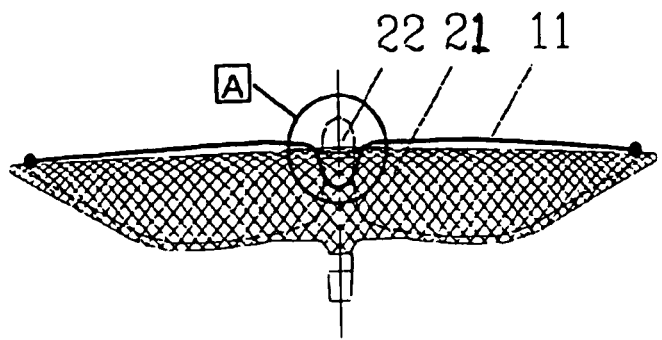
FIG. 4 is a side view of the occlusion device in accordance with the invention.

The present invention provides a heart septal defect occlusion device for occluding an anatomical aperture, such as a patent foramen ovale occluder shown in FIGS. 2 and 4. The occluder comprises a right disc 21 (which can be a metal mesh disc), tip 22, joint 23, and left disc 1 which is covered with membranes, and membranes 100, as shown in FIG. 1 and FIG. 9.

Figure 3:
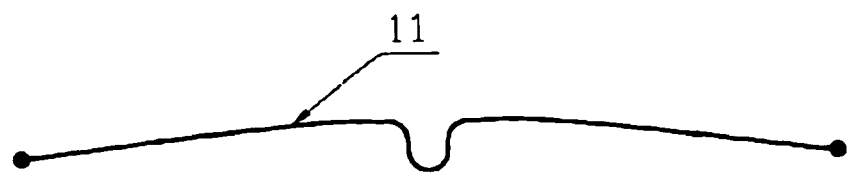
FIG. 3 is a side view of the skeleton in accordance with the invention.
Figure 11:
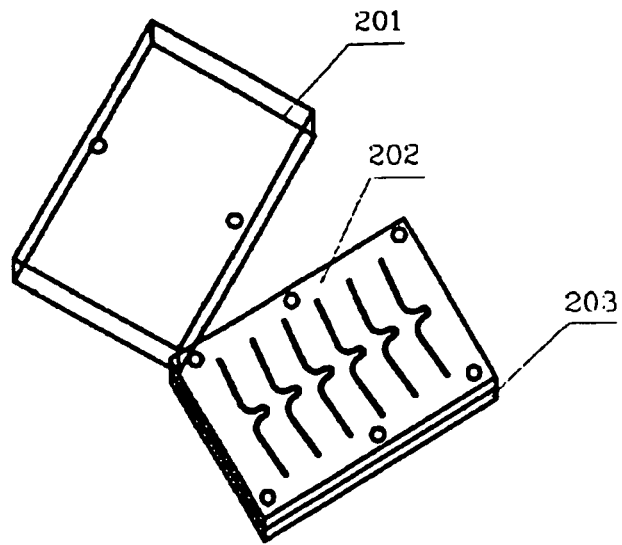
FIG. 11 is a schematic representation of a mould, which is used to heat-treat the skeletons.

The present invention will be described using a PFO occluder as an example. The maximal character of the PFO occluder, when compared with those of the above-referenced patents, is that the left disc 1 comprises six skeletons 11 which are spaced apart evenly. And the six skeletons are linked together in the center and form a radially-extending disc. It is possible that the left disc 1 may comprise at least two skeletons 11 as shown in FIG. 3, and skeleton 11 is made from nitinol wire with shape memory. FIG. 11 illustrates the mould which is used to heat treat skeletons 11. The mould includes upper-mould 201, middle-mould 202 and under-mould 203 and the nitinol wire will be put into the rabbet of the middle-mould 202. By heating the nitinol wire above a certain phase transition temperature, the crystal structure of the nitinol wire can be reset in the austenitic phase, and this will tend to "set" the shape of the device, (i.e., it can keep the shape when it is fixed in the mould). Except for an outside force, the wire can keep the "set" shape even if cooled, and when the outside force is withdrawn, it can resume its original shape. The middle segment of the skeleton 11 is U-shaped, and the depth of each U-trough is different. By providing different depth U-troughs for each skeleton 11, these skeletons can form a plane after they have been overlapped together. The skeletons 11 are then covered with membranes to form the left disc 1. The right disc 21 of the PFO occluder uses moulding components. First, the suitable tubular metal mesh of the PFO occluder is formed by weaving or laser carving, then the tubular metal mesh is inserted into the mould and undergoes heat treatment. The tip 22 and joint 23 are then welded to the disc as shown in FIG. 2.

Figure 5:
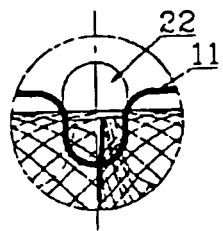
FIG. 5 is an enlarged partial sectional view of part A as shown in FIG. 4.
Figure 6:
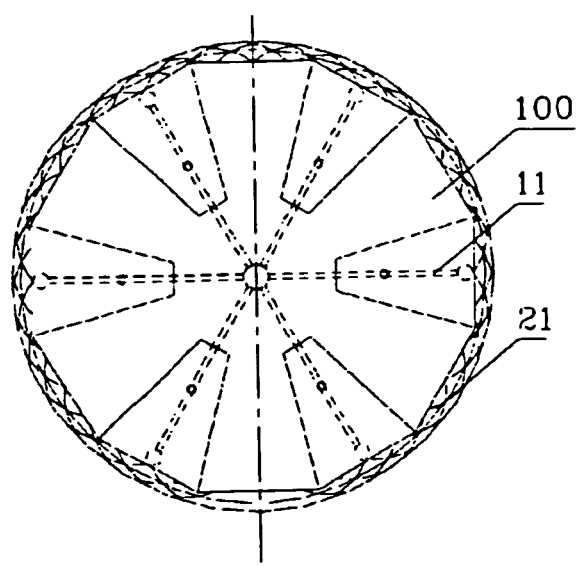
FIG. 6 is a front view of the occlusion device in accordance with the invention.

After the two ends have been welded into spheres respectively, the skeleton 11 as shown in FIG. 3 is passed through the right disc 21 and near the tip 22, and then a double-disc structure is formed as shown in FIG. 5. And as shown in FIG. 6, the skeletons 11 are spaced apart evenly. Accordingly, these skeletons 11 form a metal disc as shown in FIG. 4.

Figure 9:
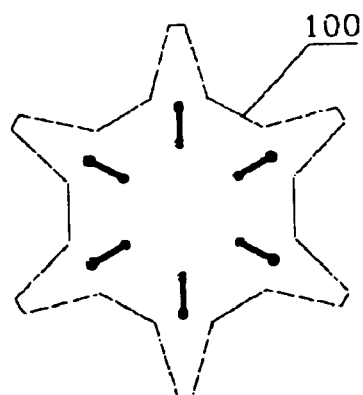
FIG. 9 is a side view of the membrane, which is used to cover the skeletons in accordance with the invention.
Figure 10:
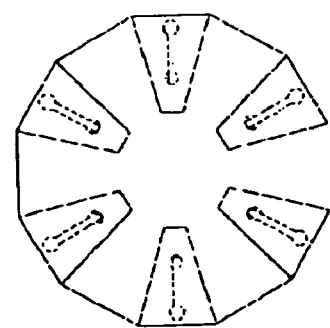
FIG. 10 is a side view of the skeletons, which have been covered with membranes such as shown in FIG. 9.

The two sides of the left disc 1 are covered with membranes 100 as shown in FIG. 9, and FIG. 10 illustrates the skeleton 11 with covered membranes 100. The membranes are made from biocompatible materials. As described above, the spheres of each skeleton are wrapped in the biocompatible materials, so that it can prevent skeleton 11 from puncturing the membranes 100. Another membrane made by biocompatible material 24 is filled into the right disc 21.

Figure 7:
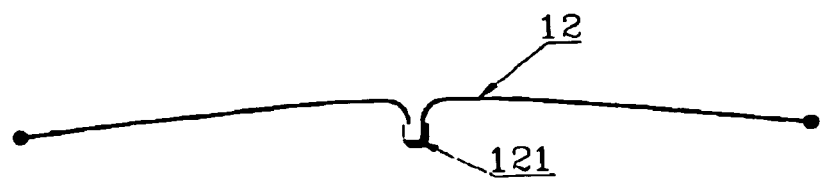
FIG. 7 and FIG. 8 are alternative embodiments of skeletons.
Figure 8:
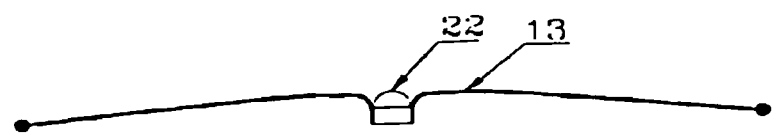

As described above, the overlapping point of left disc 1 is passed through right disc 21, and the connection between the two discs has a gimbal function. Furthermore, the two discs have a tendency of shrinking toward the inside, and the occlusion device may swing randomly; i.e., the left disc 1 and right disc 21 may be parallel or be angled. Accordingly, the device can adapt to the unique anatomy in a patient, and the two discs can be attached to the defect closely. Additionally, alternative structure and assembly of the skeleton 11 are shown in FIG. 7 and FIG. 8. FIG. 7 illustrates another embodiment of a skeleton 11 having a plurality of separate spokes 12 connected (e.g., by welding or clamping) to a central cap 121, while FIG. 8 illustrates yet another embodiment where a plurality of spokes 13 are attached directly on a tip 22 which can be the same as the tip 22 shown in FIGS. 2, 4 and 5.

The occlusion device as described above may be extended and put into a catheter, and is delivered to the desired location, then is released. The tapered waist of the device not only ensures its self-centricity but also can reduce the probability of bad occlusion effect resulting from selection error. The left disc 1, which comprises skeletons and membranes, can decrease metal surface areas, thereby decreasing thrombus formation as well as harmful elements. The two discs are both individual components and can deploy completely after release of the occlusion device, and this can avoid forming a cucurbit shape and increase the reliability of the desired occlusion.

Figure 12:
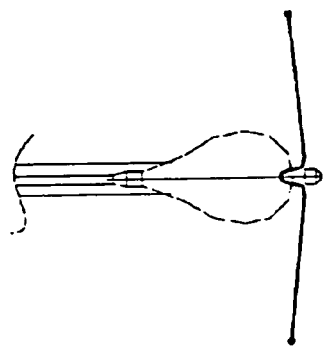
FIG. 12 is a schematic representation of a PFO occluder being released from a delivery catheter.
Figure 13:
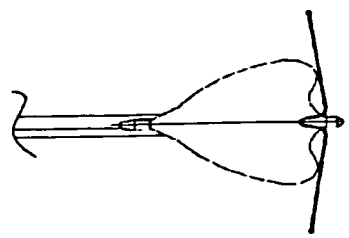
FIG. 13 is a schematic representation of an ASD occluder being released from a delivery catheter.

FIG. 12 and FIG. 13 illustrate the deployment process of an FPO occluder and an ASD occluder during operation respectively. Moreover, the occluder has excellent self-centricity because the right disc 21 is close to the left disc 1.

The present invention is also suitable for treating PDA and VSD etc. The only difference from the above other occluders is that the metal mesh of the PDA occluder of the present invention will not form a disc, but a "waist".

Figure 14:
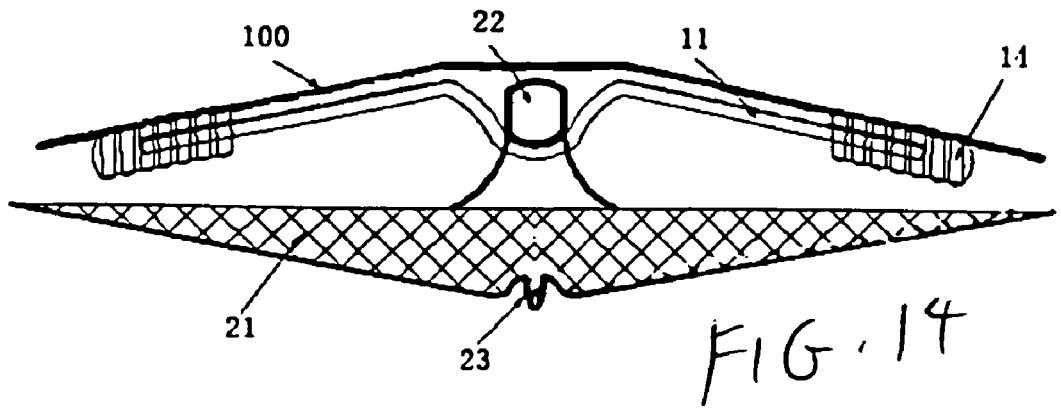
FIG. 14 is a side view of an occlusion device according to another embodiment of the present invention.

FIG. 14 illustrates a modified occlusion device where the primary change is in the construction of the skeleton. A soft coil 14 is attached to both end segments of each skeleton 11 so that the coil 14 wraps the end segment like an envelope. For instance, the coil 14 can be wound with a stainless steel wire, and its outer (i.e., distal) end is welded with the corresponding end of the skeleton 11. The length of each coil 14 can be selected between 10-80% of the length of half of the skeleton 11 (since each half of a skeleton 11 has a separate coil 14), and its pitch is carefully chosen to adjust its flexibility. As used herein, the term "pitch" P refers to the distance between adjacent windings of the coil 14. The coil 14 has a larger thickness than the thickness of the skeleton 11, thereby increasing the contact surface area between the coil 14 and the heart tissue covered by the left disc 1. This increased contact surface area reduces the injury risk to the tissue by the end segments of the skeletons 11. In other words, providing the coils 14 at the end segments of the skeleton 11 increases the contact surface area between the left disc 1 and the heart tissue. In addition, each end segment of the skeleton 11 has improved elasticity because a coiled wire is softer than when the wire is in a straightened configuration. Compared with the embodiment of FIG. 4, the construction of the skeleton shown in FIG. 14 otherwise remains unchanged, including the skeletons 11, the membrane 100, the joint 22, the tip 23, and the metal mesh disc 21.

The coils 14 provide a number of benefits. First, as mentioned above, the coils 14 provide increased contact surface area. Second, the coils 14 allow for the flexibility of each skeleton 11 to be varied. Third, the coils 14 provide resistance to breakage of the skeletons 11. In this regard, even if the wire(s) that make up the skeletons 11 were to break, the coil 14 at the broken skeleton segment provides protection because the coil 14 itself is not as susceptible to fracture or breakage.

Figure 15:
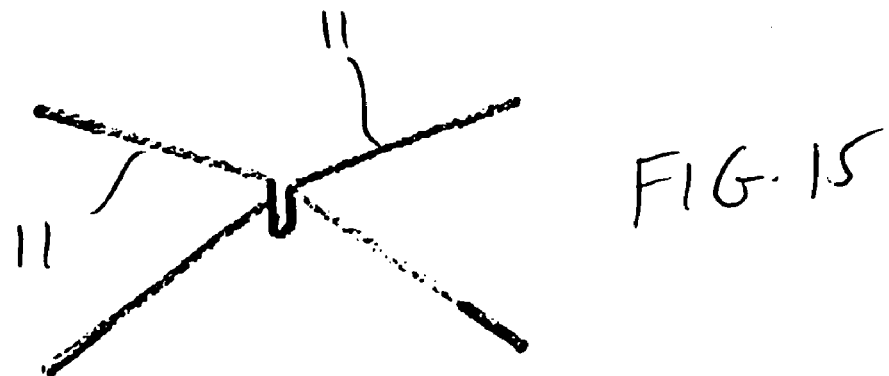
FIG. 15 illustrates two crossing skeletons of an occlusion device according to yet another embodiment of the present invention.
Figure 16:
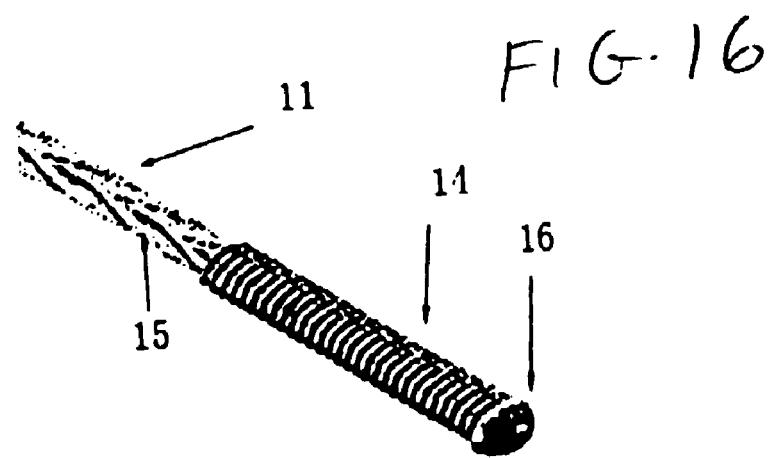
FIG. 16 is an enlarged view of one end of a skeleton of the device of FIG. 15.

More modifications for the skeleton of the present invention can be provided as illustrated below. For example, FIG. 15 illustrates an embodiment having two crossing braided skeletons, with FIG. 16 showing the details of the end part of one such skeleton. Instead of the single-wire skeleton 11 shown in FIGS. 1-14, the skeleton 11 can be braided with individual wires 15, with six or seven individual wires being a preferred embodiment. The braided skeletons shown in FIGS. 15 and 16 achieve higher fracture resistance, fatigue life and flexibility, and enable easier and more stable suture attachment for the membrane than the single wire skeletons described above. In particular, if a single wire and a multiple-wired strand are all made from the same material and having the same total cross-sectional area, the strand will normally display a higher degree of flexibility and fatigue resistance than a single wire. In addition, a single-wire has a smooth surface throughout (as compared to a braided strand), thereby providing fewer locations for suturing the membranes. The coil 14 is wound tightly before the braided strands of the skeleton 11 are passed through the cavity or bore of the coil 14. As best seen from FIGS. 15 and 16, the outer end of the coil 14 can be welded to the end of the braided strand to form a spherical end 16.

Figure 17:
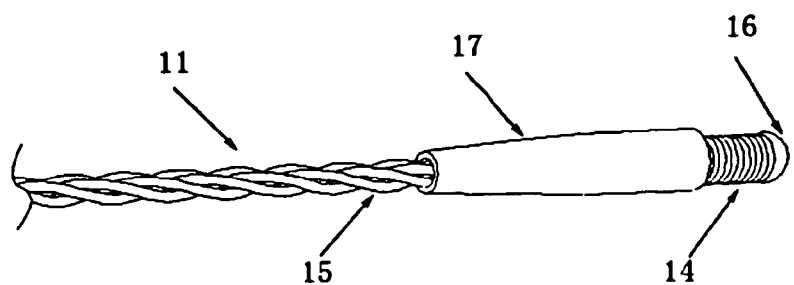
FIG. 17 illustrates a modification that can be to the skeletons of FIGS. 14 and 15.

FIG. 17 illustrates another modification that can be made to the skeletons shown in FIG. 14 or 15+16. In FIG. 17, the inner end of the coil 14 can be wrapped with an ePTFE tape 17, in order to avoid friction between the extruding end of the coil 14 and the tissue, and to reduce the level of allergy for the tissue that contacts the skeletons 11. The tape 17 can be rolled like a thin tube. As a result, the coil 14 is positioned around the braided strand (as shown) or the single wire (not shown) of the skeleton 11, and the ePTFE tape 17 is positioned around a part of the coil 14.

Figure 18:
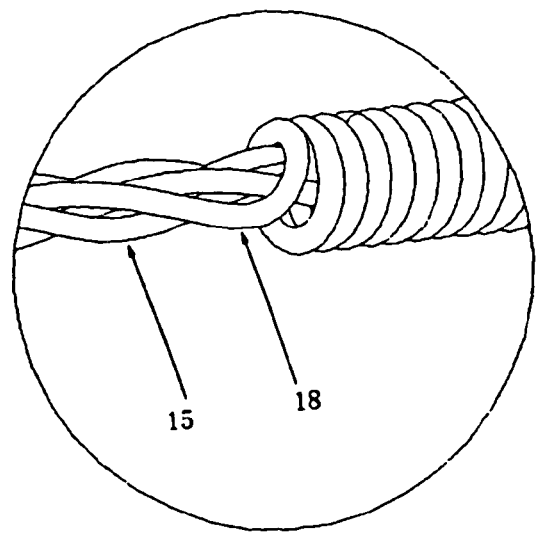
FIG. 18 is an enlarged view of one end of a skeleton of the device of FIG. 15 with the coil wound in a forward direction.

When the middle part of the skeleton 11 is braided using individual wires 15, as shown in FIG. 18, a single wire 18, which is one of the individual wires 15, can be picked up from the braided strand to wind the coil 14 around the strand. In FIG. 18, the other wires 15 in the strand extend to the end of the skeleton 11, while the single wire 18 is picked up before the end of the skeleton 11 and wound around the braided strand in a forward direction (i.e., distally towards the end of the skeleton 11) to form the coil 14. Finally, at their common end, the coil 14 and the braided strand are welded together to form the spherical end 16. Thus, this construction and method is even easier than providing the coil 14 and the skeleton 11 as separate components, and then compressing them together during welding. On the other side of the skeleton, another wire (such as 18) can also be picked up from the strand and the other end segment is also braided with the other wires 15, and the coil 14 can be formed in the same way. Since both the strand and the coils 14 are made from the same metal (e.g., Nitinol), local galvanic corrosion will be eliminated from this part of the skeleton 11. More importantly, such unique integration of the skeleton 11 creates a reliable connection between the wires of the skeleton 11 and the coils 14. Therefore, long term durability of the left disc 1 is greatly enhanced.

Figure 19:
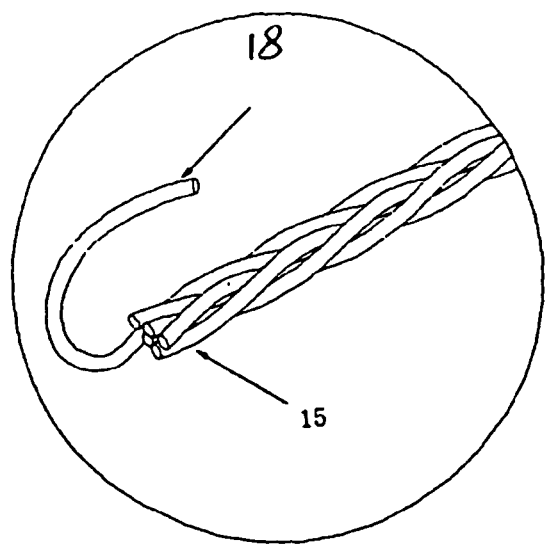
FIG. 19 is an enlarged view of one end of a skeleton of the device of FIG. 15 with the coil wound in a rearward direction.

As an alternative, as shown in FIG. 19, the single wire 18 can be picked up from the stand when the strand braid is finished. More specifically, the single wire 18 is separated from the other five wires 15 of the same strand, and extends away from the end of the strand braid. The single wire 18 is wound rearwardly (i.e., proximally) from the end of the braided strand to wind the coil 14 which wraps around the end segment of the braided strand. FIG. 20 illustrates the completed coil 14 for the method shown in FIG. 19. Both embodiments of FIGS. 18 and 19 ensure that the coil 14 will not be separate from the strand, thereby forming a solid skeleton 11.

The braided strands can extend through varying lengths of the coil 14, as illustrated in FIGS. 21A-21C, to achieve varying flexibility for the end segments of the skeletons 11. For example, FIG. 21A illustrates the strand braided with the wires 15 extending through the entire length of the bore of the coil 14 and having its end attached (e.g., by welding) to the spherical end 16 which is also attached (e.g., by welding) to the end of the coil 14. FIG. 21B illustrates the strand braided with the wires 15 extending through part of the length of the bore of the coil 14, which can be formed with one of the wires 15 as shown in FIG. 18. In FIG. 21B, the spherical end 16 is attached (e.g., by welding) to the end of the coil 14. FIG. 21C illustrates the strand braided with the wires 15 terminating near the inner (i.e., proximal) end of the coil 14, but having at least one wire 19 extending through part of the length of the bore of the coil 14 which can be formed using one of the wires 15 as shown in FIG. 18. In FIG. 21C, the spherical end 16 is attached (e.g., by welding) to the end of the coil 14. Alternatively, the wire 19 can further extend to weld with the coil 14 at the spherical end 16, or still further extend to wind the coil 14 rearwardly as shown in FIG. 19 instead of picking up one of wires 15 to wind the coil 14 forwardly.

There are situations where the left disc 1 may have difficulty conforming to the heart anatomy with minimum injury risk. For example, some complicated heart structure defects, such as PFO, can cause a skewed or pulsed configuration for the left disc 1 of the occlusion device, so operation risk arises due to the U-shaped segments of the skeletons 11 shown above. As each skeleton arm is individually contacted with the tissue and forced to bend outside of the occlusion device, the U-shaped segments may deform asymmetrically, and experience high local tension. However, as reflected by FIGS. 1 and 5 above, several U-shaped segments and the joint 22 are already crowded together, thereby allowing little space for them to get closer. When the U-shaped segments bend against the joint 22, the joint 22 will block the U-shaped segments from deforming further and also resist the movement of the skeletons 11, resulting in greater reaction force on the tissue in contact with the resisting skeletons 11. This excess pressure can cause serious injury to the heart, such as atrial fibrillation. To prevent this difficult situation, the shape of the middle segments can be modified to increase flexibility, as shown in FIG. 22, where the U-shaped segment is replaced by a looped section 28 where the skeleton 11 is twisted or looped to cross or overlap itself. When the skeleton arms bend in the same direction, as shown in FIG. 23, the joint inside the looped section 28 will not hinder the looped section 28 and the skeleton arms. With carefully chosen loop sizes, several looped sections 28 can be nested within each other in a manner to form a mutually locking structure for a full set of skeletons 11 for a left disc 1. As shown in FIG. 24, two looped skeletons cross and lock each other. Thus, the looped sections 28 allow easier bending of the skeletons 11 than the U-shaped segments, thereby significantly reducing the reaction force on the tissue and the associated injury risk.

The occlusion device of the present invention can optionally combine different features of the above embodiments to utilize multiple advantages. For example, the skeletons with looped sections, braided strands and coiled ends can produce higher flexibility and minimize injury risk. All metallic parts of the occlusion device can be coated with biocompatible materials, such as titanium nitride thin film, which facilitates endothelialisation and reduces thrombus risk. In addition, providing a sufficient thickness of ceramic coating can also reduce the harmful nickel release from Nitinol.

While the description above refers to particular embodiments of the present invention, it will be understood that many modifications may be made without departing from the spirit thereof.

What is claimed is:

1. A heart septal defect occlusion device, comprising:
   a right disc made from an interwoven metal mesh, the metal mesh having a plurality of openings; and
   a left disc comprising at least two skeletons that form a plane when deployed, and that are covered by a membrane, with each skeleton passing through openings of the metal mesh to interlock the right and left discs, wherein the left disc is different from the right disc, wherein each skeleton has opposing end segments, with a coil wrapped around and directly connected to each end segment; and
   wherein the right and left discs are individual components that can deploy completely after releasing to avoid forming a cucurbit shape.

2. The device of claim 1, wherein the length of the coil is between 10% to 80% of the length of half of the respective skeleton.

3. The device of claim 1, wherein the each coil has a thickness that is greater than the thickness of the skeleton.

4. The device of claim 1, wherein each coil has a distal end, and a spherical end is provided at the distal end of the coil.

5. The device of claim 1, wherein each coil has a distal end, and each end segment of the skeleton is attached to the distal end of the respective coil.

6. The device of claim 1, wherein an ePTFE tape is positioned around a part of each coil.

7. The device of claim 1, wherein each skeleton is formed from a braided strand of a plurality of wires.

8. The device of claim 7, wherein each coil is formed by extending one wire from the plurality of wires, and winding the one wire to form a coil.

9. The device of claim 8, wherein the one wire is wound in a forward direction to form the coil.

10. The device of claim 8, wherein the one wire is wound in a rearward direction to form the coil.

11. The device of claim 7, wherein a portion of the end portion is formed with some but not all of the wires of the braided strand, and the coil extends over the portion of the end segment that is formed with some but not all of the wires of the braided strand.

12. The device of claim 11, wherein each end segment has only one wire extending through the entire length of the respective coil and attached to the a distal end of the respective coil.

13. The device of claim 1, wherein the left disc is made from at least two radial skeletons.

14. The device of claim 1, wherein the skeletons define two sides, and the skeletons are covered with membranes on both sides.

15. The device of claim 1, wherein each skeleton having a looped section where the skeleton is twisted or looped to cross or overlap itself.

16. The device of claim 1, wherein each skeleton and the coils are formed from the same material.

17. The device of claim 1, wherein the coils and the skeletons are made from nitinol and coated with titanium nitride thin films.

18. A heart septal defect occlusion device, comprising:
   a right disc made from an interwoven metal mesh, the metal mesh having a plurality of openings; and
   a left disc comprising at least two skeletons that form a plane when deployed, and that are covered by a membrane, with each skeleton passing through openings of the metal mesh to interlock the right and left discs, wherein the left disc is different from the right disc, each skeleton having a single looped middle section where the skeleton is twisted or looped to cross or overlap itself and extends around itself towards an opposite direction; and
   wherein the right and left discs are individual components that can deploy completely after releasing to avoid forming a cucurbit shape.

19. The device of claim 18, wherein the left disc is made from at least two radial skeletons.

20. The device of claim 18, wherein the skeletons define two sides, and the skeletons are covered with membranes on both sides.

* * * * *